US00PP34736P2

(12) United States Plant Patent
Leis

(10) Patent No.: US PP34,736 P2
(45) Date of Patent: Nov. 15, 2022

(54) STRAWBERRY PLANT NAMED 'CIVL519'

(50) Latin Name: ***Fragaria* x *ananassa* Duchesne ex Rozier**
Varietal Denomination: CIVL519

(71) Applicant: C.I.V.—CONSORZIO ITALIANO VIVAISTI—SOCIETÀ CONSORTILE A R.L., Comacchio (IT)

(72) Inventor: Michelangelo Leis, Ferrara (IT)

(73) Assignee: C.I.V.—CONSORZIO ITALIANO VIVAISTI—SOCIETÀ CONSORTILE A R.L., Comacchio (IT)

( * ) Notice: Subject to any disclaimer, the term of this patent is extended or adjusted under 35 U.S.C. 154(b) by 0 days.

(21) Appl. No.: 17/736,729

(22) Filed: May 4, 2022

(30) Foreign Application Priority Data

May 5, 2021 (QZ) ..... PBR 2021/1224

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208, 209
See application file for complete search history.

*Primary Examiner* — Susan McCormick Ewoldt
(74) *Attorney, Agent, or Firm* — Foley & Lardner LLP

(57) ABSTRACT

This invention relates to a new and distinct variety of strawberry plant named 'CIVL519'. This new strawberry plant named 'CIVL519' is primarily adapted to the climate and growing conditions of Mediterranean and subtropical areas, and is primarily characterized by plants with compact leaves and visible fruits; easy to collect; fruits with regular and conical shape; easy to pollinate; excellent firmness consistency; and great taste with high sugar content and aroma.

4 Drawing Sheets

Latin name of the genus and species of the plant claimed: *Fragaria* x *ananassa* Duchesne ex Rozier.

Variety denomination: 'CIVL519'.

CROSS-REFERENCE TO RELATED APPLICATION

This application claims priority from Community Plant Variety Rights Application No. 2021/1224, filed May 5, 2021.

BACKGROUND OF THE INVENTION

The present invention relates to a new and distinct strawberry variety named 'CIVL519'. The variety is botanically known as *Fragaria* x *ananassa* Duchesne ex Rozier.

The new strawberry 'CIVL519' is a product of a planned breeding program conducted by the inventors, Michelangelo Leis in San Giuseppe di Comacchio, Ferrara, Italy. The objective of the breeding program is to develop a new strawberry variety with high resistance to leaf and root disease. Fruits with regular and conical shape, bright colour, excellent consistence, good taste and aroma even high temperatures.

This new strawberry 'CIVL519' is a result of a controlled cross made by the inventors in 2013, in San Giuseppe di Comacchio, Ferrara, Italy. The female or seed parent is strawberry variety designated 9E1D-19 (unpatented CIV's selection). The male or pollen parent is strawberry variety designated 5F1I-1 (unpatented CIV's selection).

The new strawberry 'CIVL519' was discovered and selected by the inventor as a single flowering plant within the progeny of the stated cross in May 2016 in San Giuseppe di Comacchio, Ferrara, Italy (44° 45' North and 12° 11' East). After its selection, the new variety was asexually propagated by stolons in a nursery located in San Giuseppe di Comacchio, Ferrara, Italy. The new variety was extensively tested over the next several years in different European area with low chill condition. This propagation has demonstrated that the combination of characteristics as herein disclosed for the new cultivar are firmly fixed and retained through successive generations of asexual reproduction. The new cultivar reproduces true to type.

BRIEF SUMMARY OF THE INVENTION

'CIVL519' is primarily adapted to the climate and growing with low chill condition. This area provides the needed and correct temperatures for flower induction, and to produce a strong and vigorous plant, and to maintain fruit quality during full production.

The following traits have been repeatedly observed and are determined to be unique characteristics of 'CIVL519', which in combination distinguish this strawberry plant as a new and distinct variety:

1. plants with compact habit and visible fruits;
2. easy to collect;
3. fruits with regular and conical shape;
4. easy to pollinate;
5. excellent consistency; and
6. great taste with high sugar content and aroma.

Plants of the new strawberry variety 'CIVL519' differ from plants of the parents, 5F1I-1 and 9E1D-19 in the characteristics described in Table 1.

TABLE 1

| Characteristic | 'CIVL519' | 5F1I-1 | 9E1D-19 |
|---|---|---|---|
| Time of ripening | Very early to early | Medium | Early |
| Grow habit | Semi-upright | Upright | Semi-upright |
| Plant vigour | Weak | Medium | Medium to strong |
| Fruit size | Large to very large | Medium | Large |
| Firmness | Strong | Firm | Medium |
| Sweetness | Higher | Medium to high | Medium |

Of the many commercial cultivars known to the present inventor, the most similar in comparison to the new strawberry variety 'CIVL519' is the strawberry variety VENTANA. Plants of the new strawberry variety 'CIVL519' differ from plants of strawberry variety VENTANA in the characteristics described in Table 2:

TABLE 2

| Characteristic | 'CIVL519' | VENTANA |
|---|---|---|
| Grow habit | Semi-upright | Semi-upright |
| Plant vigour | Weak | Medium |
| Fruit size | Large to very large | Large |
| Firmness | Strong | Medium |
| Sweetness | Higher | Medium |
| Time of beginning of flowering | Very early | Early |
| Time of beginning of ripening | Very early | Early |

BRIEF DESCRIPTIONS OF THE PHOTOGRAPHS

The accompanying color photographs illustrate the overall appearance of typical specimens of the new strawberry variety 'CIVL519', at various stages of development as true as it is reasonably possible with color reproductions of this type. Color in the photographs may differ slightly from the color value cited in the botanical description which accurately describe the color of 'CIVL519'. The depicted plant and plant parts of the new strawberry variety 'CIVL519' were taken in Battipaglia, Salerno, Italy, and are approximately 6 to 9 months old.

DETAILED BOTANICAL DESCRIPTION

Figure 1:
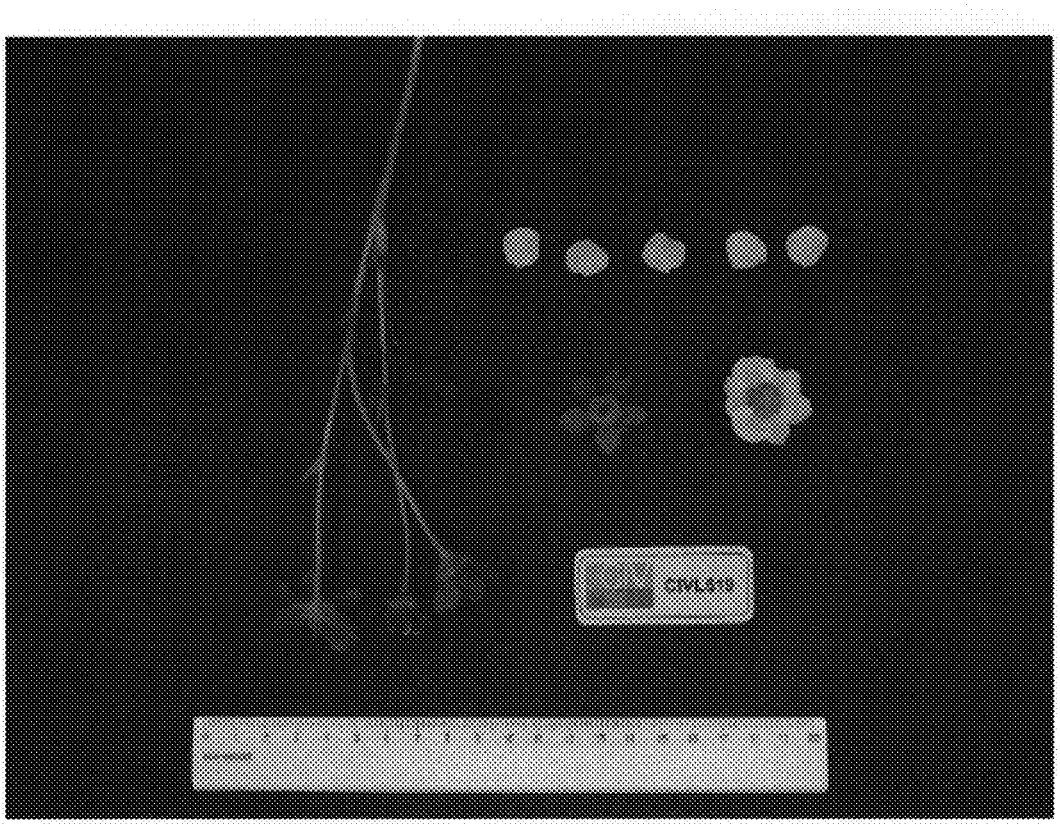
FIG. 1 shows typical flowers of 'CIVL519'.
Figure 2:
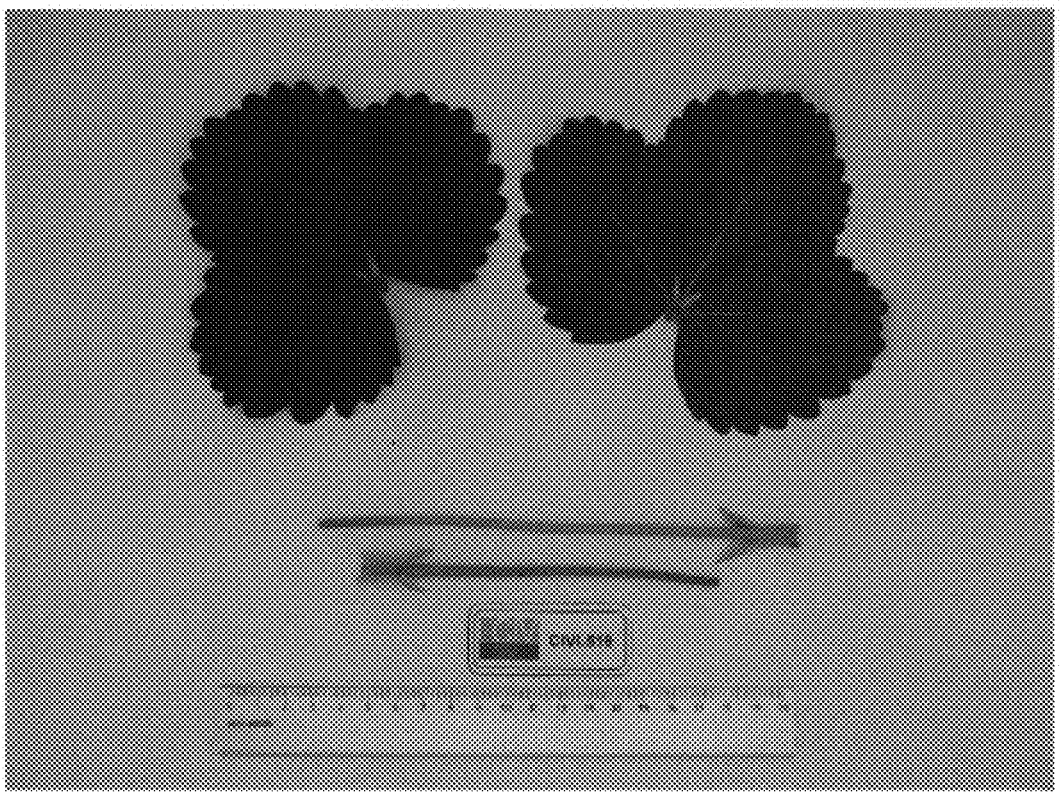
FIG. 2 shows the leaves of 'CIVL519'.
Figure 3:
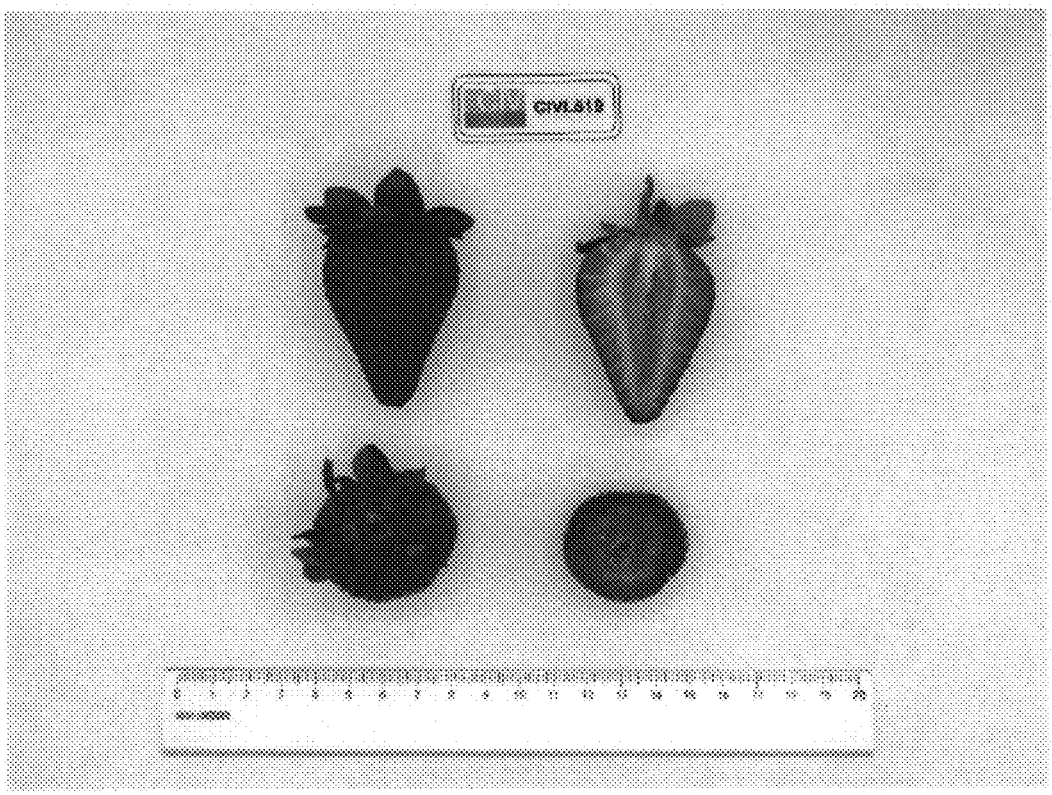
FIG. 3 shows typical fruits of 'CIVL519'.
Figure 4:
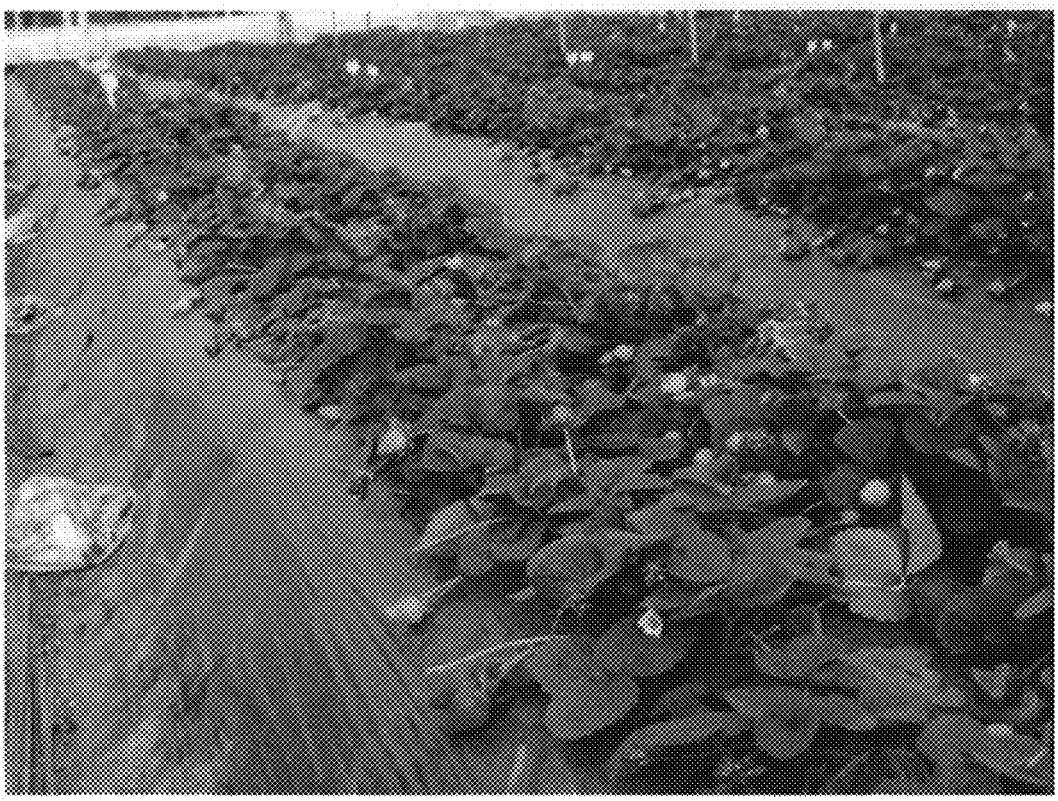
FIG. 4 shows plant of 'CIVL519'.

'CIVL519' has not been observed under all possible environmental conditions. The characteristics of the new variety may vary in detail, depending upon variations in environmental factors, including weather (temperature, humidity and light intensity), day length, soil type and location.

The aforementioned photographs, together with the following observations, measurements and values describe the new strawberry variety 'CIVL519', unless otherwise noted, taken during March 2020 growing season in Battipaglia, Salerno, Italy. The observations, measurements and values were taken from plants of 'CIVL519' dug from Vivai Mazzoni Polska sp.z.o.o., Regon 240016883, kostomloty II 29, 21-509 Koden-Polonia, during October 2019 and planted approximately in the same month in CIV's test fields in Battipaglia, Salerno, Italy. Plants of the new strawberry variety 'CIVL519' were grown under conditions which closely approximate those generally used in commercial practice. The observed plants were one year old plants. The plants used in the production field are produced in a nursery in Vivai Mazzoni Polska sp.z.o.o., Regon 240016883, kostomloty II 29, 21-509 Koden-Polonia.

Yield observations and fruit quality characteristics are averaged from 2019 of data collected from the 2019 through 2021 growing seasons. Flower measurements and characteristics are from secondary flowers unless otherwise noted. Fruit characteristics and measurements are from secondary fruit unless otherwise noted.

Color references are made to The Royal Horticultural Society Colour Chart (R.H.S.), except where general colors of ordinary significance are used. Color values were taken under daylight conditions at approximately 3 pm in Battipaglia (SA) Italy. The approximate age of the observed plants is about 12 months.

The following tables 3-9 describe fruit, plant, stolon, foliage, fruiting truss, flower and pest/disease characteristics of the new strawberry 'CIVL519'.

TABLE 3

FRUIT CHARACTERISTICS

| Characteristic | 'CIVL519' |
|---|---|
| Color of mature fruit | Red group - RHS 45A |
| Color of internal flesh | Red group - RHS 41D |
| Length (cm) | About 5.5 cm |
| Width (cm) | About 3.5 cm |
| Ratio length/width | Moderately longer |
| Calyx diameter (cm) | About 4.5 cm |
| Average weight (gm) | About 23 g |
| Achene color | Yellow-green group 150C |
| Number of achenes per $cm^2$ measured at the center of berry | About 7 |
| Average weight of 1000 achenes (g) | About 0.67 g |
| Marketable yield (gm/plt) | Average 450 gm/plt |
| Size | Large |
| Predominant shape | Conical |
| Difference in shapes between primary and secondary fruit | Slight |
| Band without achenes | Absent |
| Unevenness of surface | Even or slightly uneven |
| Evenness of color | Strong |
| Glossiness | Strong |
| Insertion of achenes | Level with surface |
| Insertion of calyx | Level with fruit |
| Attitude of the calyx | Upward |
| Size of calyx in relation to fruit diameter | Slightly larger |
| Adherence of calyx | Strong |
| Firmness of skin | Firm |
| Firmness of flesh | Firm |
| Distribution of red color of the flesh | Uniform |
| Hollow center expression | Absent or small |
| Flavor | Good tase with good aroma and sugar content |
| Soluble solids (% brix) | About 9% |
| Time of first flowering | Very early |
| Time of first harvesting | Very early |
| Harvest period | From January until June in Battipaglia, Salerno, Italy |
| Type of bearing | Not remontant |

TABLE 4

| PLANT CHARACTERISTICS | |
|---|---|
| Characteristic | 'CIVL519' |
| Height (cm) | About 10 to 20 cm |
| Spread (cm) | About 30 to 40 cm |
| Size | Medium |
| Habit | Semi-upright |
| Density | Medium |
| Vigor | Weak |

TABLE 5

| STOLON CHARACTERISTICS | |
|---|---|
| Characteristic | 'CIVL519' |
| Average number per plant | About 15-20 |
| Anthocyanin coloration | Red group - 53B |
| Anthocyanin intensity | Medium |
| Diameter at bract (mm) | About 3 mm |
| Pubescence | Dense |

TABLE 6

| FOLIAGE CHARACTERISTICS | |
|---|---|
| Characteristic | 'CIVL519' |
| Foliage: | |
| Color of upper surface | Green group - 137A |
| Color of underside | Green group - 137C |
| Shape in cross section | Concave |
| Interveinal blistering | Medium |
| Glossiness | Medium |
| Number of leaflets | 3 |
| Terminal Leaflet: | |
| Length (cm) | About 6.1 cm |
| Width (cm) | About 6.5 cm |
| Length/width ratio | Equal |
| Serrations/leaf | Overlapping |
| Size | Medium |
| Shape of base | Rounded |
| Shape of teeth | Serrate to crenate |
| Petiole: | |
| Length (cm) | About 13 cm |
| Diameter (mm) | About 2.7 mm |
| Pubescence | Medium |
| Attitude of hairs | Horizontal |
| Stipule: | |
| Length (mm) | About 35 mm |
| Width (mm) | About 9 mm |
| Anthocyanin coloration | Weak |
| Color | Yellow-green group 145C |

TABLE 7

| FRUITING TRUSS CHARACTERISTICS | |
|---|---|
| Characteristic | 'CIVL519' |
| Length (cm) | About 20-25 cm |
| Attitude | Erect |
| Position relative to foliage | Above |
| Pubescence | Strong |

TABLE 7-continued

| FRUITING TRUSS CHARACTERISTICS | |
|---|---|
| Characteristic | 'CIVL519' |
| Antbocyanin intensity | Weak |
| Attitude at first pick | Horizontal |

TABLE 8

| FLOWER CHARACTERISTICS | |
|---|---|
| Characteristic | 'CIVL519' |
| Petal color | |
| Mature (upper) | White group - 155D |
| Mature (lower) | White group - 155D |
| Petal shape | |
| Overall | Transverse elliptic |
| Apex | Rounded |
| Base | Rounded |
| Petal length (mm) | About 1 to 1.5 cm |
| Petal width (mm) | About 0.80 to 1.3 cm |
| Petal length/width ratio | Moderately longer |
| Number of petals/flower | About 5 to 7 |
| Sepals color | |
| Mature (upper) | Green group - 137A |
| Mature (lower) | Green group - 138A |
| Sepal shape | |
| Overall | Narrow elliptic |
| Apex | Pointed |
| Base | Flat |
| Sepal length (mm) | From 1 to 1.5 cm |
| Sepal width (mm) | From 0.5 to 0.7 cm |
| Sepal length/width ratio | Longer |
| Number of sepals/flower | About 9 to 13 |
| Corolla diameter (mm) | About 30 mm |
| Calyx diameter (mm) | About 30 mm |
| Size of calyx relative to corolla | Equal |
| Size of inner calyx relative to outer calyx | Smaller |
| Relative position of petals | Overlapping |

TABLE 9

| REPRODUCTIVE ORGANS | |
|---|---|
| Characteristic | 'CIVL519' |
| Receptacle color | Yellow green group - 154B |
| Pollen color | Yellow orange group - 14A |
| Stamen | Present |
| Pollen amount | Much |

TABLE 10

| PEST AND DISEASE REACTIONS | |
|---|---|
| Characteristic | 'CIVL519' |
| Powdery mildew (*Sphaerotheca macularis*) | Tollerant |
| Angular leaf spot (*Xanthomonas fragariae*) | Moderately susceptible |
| Botrytis fruit rot (*Botrytis cinerea*) | Very low sensibility |
| Fusarium wilt (*Fusarium oxysporum*) | Moderately susceptible |
| Anthracnose crown rot (*Colletotrichum fragariae*) | Moderately susceptible |
| Two-spotted spider mite (*Tetranychus urticae*) | Susceptible |

I claim:

1. A new and distinct strawberry plant named 'CIVL519', as herein described and illustrated by the characteristics set forth above.

* * * * *